United States Patent [19]

Maes

[11] Patent Number: 6,090,385
[45] Date of Patent: Jul. 18, 2000

[54] METHOD OF TREATING CANCER

[76] Inventor: Hubert Maes, Anda Biologicals, 37, rue de la Course, BP 76, 67067 Strasbourg Cedex, France

[21] Appl. No.: 08/797,474

[22] Filed: Feb. 6, 1997

Related U.S. Application Data

[63] Continuation of application No. 08/353,227, Dec. 1, 1995, abandoned.

[30] Foreign Application Priority Data

Dec. 10, 1993 [BE] Belgium .............................. 093091375

[51] Int. Cl.$^7$ .......................... A61K 39/00; A61K 39/38; A61K 45/00; A61K 35/12
[52] U.S. Cl. .................................. 424/184.1; 424/278.1; 424/513; 424/520; 424/197.11
[58] Field of Search ............................. 424/184.1, 228.1, 424/513, 520, 197.11

[56] References Cited

U.S. PATENT DOCUMENTS

| | | |
|---|---|---|
| 4,504,473 | 3/1985 | Cantrell . |
| 4,505,903 | 3/1985 | Cantrell . |
| 4,543,253 | 9/1985 | Yamamura et al. . |
| 4,613,504 | 9/1986 | Cantrell . |
| 4,663,306 | 5/1987 | Cantrell . |
| 4,726,947 | 2/1988 | Shimada et al. .......................... 424/92 |
| 4,777,130 | 10/1988 | Maes . |
| 4,965,192 | 10/1990 | Maes ........................................... 435/7 |
| 5,091,308 | 2/1992 | Klegerman et sl. ................... 435/68.1 |
| 5,484,596 | 1/1996 | Hanna et al. . |

FOREIGN PATENT DOCUMENTS

| | | |
|---|---|---|
| 0657168 | 6/1995 | European Pat. Off. . |
| 2120548 | 4/1982 | United Kingdom . |

OTHER PUBLICATIONS

Maes, Klin. Wochenschr, 69:696–709, 1991.
Maes et al, Scand. J. Immunol. 41:53–64, 1995.
Closs et la. Scand. J. Immunol. 12:249–63, 1980.
Pines, Lancet, Feb. 21, 1976 pp. 380–381, 1976.
Beaudet et al, Ann. Immunol. 134 C: 216–26, 1983.
Hanna et al, J. Nat'l Cancer Inst. 51:1897–1908, 1973.
Encyclopedia of Biochemistry Ed. Williams & Lansford pp. 735–736, pp. 589–91, 1967.
Lou et al, Anticancer Research, 14: 1469–1476, 1994.
Cocito et al. Med. Microbiol Immunol. 177: 357–367, 1988.
Lomakin et al, Byulleten' Eksperimental 'noi Biologii i Meditsiny 83/1: 65–68, Jan. 1977.
Merck Manual, Home Edition p. 887, 1997.
Cocito et al, Clin. Exp. Immunol, 66:262–272, 1986.
Wainberg et al, Br. J. Cancer, 34: 500–508, 1976.
Pinsky et al, Natl Cancer Inst. Monogr. 39: 225–228, 1973.
Mathe et al, Natl Cancer Inst. Monogr. 39: 165–175, 1973.
Gueur et al, Scand. J. Immunol. 17: 497–506, 1983.
Immunobiology for the Clinician Ed: Barber. p. 241, 1977.
Dunlap et al, Tuberculosis, 77/6: 1235–1251, 1993.
Bennett et al, Cancer Research 43: 4183–4190, 1983.

McKneally et al Lancet May 7, 1977 p. 1003, 1977.
Coltsier et al, Clin. & Diagnost.Lab.Immunol. 1/2: 139–144, 1994.
Duda et al Cancer Researcher Weekly May 2, 1994 Abstract Only, 1994.
Morales et al. J. Urology, 116: 180–183, 1976.
Codish et al. J. Surgical Oncology 10: 447–455, 1978.
Parr, Cancer Immunol. Immunother. 1:51–53, 1976.
Sparks et al. New Eng. J. Med. 289:287–830, 1973.
Baldwin et al. Ann. N.Y. Acad. Sciences 277: 124–134, 1976.
Nathanson, Seminars in Oncology 1/4: 337–350, 1974.
Bruneteau et al. 1992. Composition and Immunogenicity of the Polysaccharide Components . . . Med. Microbiol, Immunol. 181. 13–23.
Hubbard et al. 1992. Immunization of Mice with the Antigen A6D of *Mycobacteruim boris* BCG. Clin. Exp. Immunol. 88: 129–131.
Yasumoto et al. 1979. Nonspecific Adjuvent Immunotherapy of Lung Cancer . . . Cancer Res. 39: 3262–67.
Beschin et al. 1991. Mycobacterial Proliferation in Macrophage is Prevented . . . Eur. J.Immunol. 21: 793–797.
Benoit et al. 1989 Delayed Hypersensitivity Reactions by the Mycobacterial Antigen A6O . . . Med Microbiol Immunol.178: 105–112.
Cocito et al. 1991. Properties of the Mycobacterial Antigen Complex A6O and its Applications . . . Chest. 100(6): 1687–1693.
Yamamura et al. 1978. Mycobacteria and Cellular Immunity. Tuberculosis (Tokyo) 53/11 :551–554 Abstract only.
Carlucci, et al. 1993. Mycobacterial Antigen A6O–Specific T–Cell Reperrtorie . . . Infection and Immunity.61(2):439–447.
Groves, 1993. Pharmaceutical Characterization of *Mycobacleruim boris* . . . J. Pharmaceutical Sciences. 82(6): 555–562.2.
Abou–Zeid et al. 1985, Cross–Reactivity of Antigens from the Cytoplasm and Cell Walls . . . J. Infectious Dis. 151(1): 170–178.
Pang et al. 1982 Immunioprophylaxis of a Murine Bladder Cancer with High . . . J. of Urology. 127(5): 1006–1009.
Yamamura et al. 1976. Immunotherapy of Cancer with Cell Wall Skeleton . . . Ann. N.Y. Acad. Sci. 277: 209–227.
Kaplan et al. 1980. Cancer 46: 2195–2202.

*Primary Examiner*—Nita Minnifield
*Attorney, Agent, or Firm*—William J. Daniel

[57] ABSTRACT

A method of treating cancers by administering to a patient an anti-tumor effective amount ot at least one of a thermostable macromolecular antigen complex or a fragment of such a complex which is interspecific for microorganisms of the Mycobacteria, Nocardia and Corynebacteria group and which exhibits after immunoelectrophoresis an immunoelectrophoretic precipitation pattern corresponding to that of the antigen complex 60 of *Mycobacteria bovis* Calmette Guerin Bacillus strain. Preferably, the patient is also treated with an additional therapeutic agent which is specific against the patient's cancer such as a tumoral antigen or a non-proliferative tumor cell.

9 Claims, No Drawings

METHOD OF TREATING CANCER

This application is a continuation-in-part, of application Ser. No. 08/353,227, filed Dec. 1, 1995 now abandoned.

FIELD OF THE INVENTION

The present invention concerns a method of treating and/or preventing cancer.

BACKGROUND OF THE INVENTION

Among the treatments for cancer, chemotherapy and radiotherapy are very efficacious means for the primary elimination of leukemias, neoplasms and tumors, whereas surgery allows the excision of solid tumors. However, the prolongation of the life expectancy of patients successfully treated is often not satisfactory because of relapses.

Immunotherapy used as an antitumoral weapon derives from the need of treatments complementary to chemotherapy which, if the kinetics of first order is followed, is theoretically unable to eradicate "the last subsisting tumoral cell".

Remissions of a breast, prostate or lung carcinoma after surgery, irradiation or chemotherapy may last from 5 to 25 years, followed by relapse. As long as the immune system of the patient in remission functions normally and is not unduly solicited, the remaining tumor cells subsisting in the organism of the patient after a primary intervention will stay controlled and will not induce a relapse.

Tumor cells escape the immunological surveillance of the host by diverse mechanisms, of which the best known are, on the one hand, the scarcity of tumoral antigens that would allow for the recognition of the neoplasm by the immune system of the host and, on the other hand, the capacity of cancers to drastically reduce the immune defenses of this host. When the balance is tilted in favour of the host, at the expense of the tumor, the immunological defense mechanisms become efficient.

An immunotherapeutic intervention may reasonably find its place in a scheme of treatment only in case of recently implanted tumors (M. McKneally et al.: The Lancet, May 7 (1977), page 1003), of early diagnosed tumors of small size or of reduced numbers of cells, or after a prior intervention (surgery, chemotherapy, irradiations) has reduced the size of the tumor or the number of leukaemic cells to a proportion that would allow the immune system to regain control (N. Gross and A. Eddie: Am. Rev. Resp. Dis., 113, p. 457–464 (1976); G. Mathé et al.: Nat. Cancer Inst. Monograph No. 39, p. 165–175 (1973)).

The rejection of neoplasms by immunological means is partly based on a specific immune recognition of this neoplasm. This specific immunotherapeutic approach exploits the existence of tumor cell surface antigens recognizable by the immune system of the patient. In practice, this method may be undertaken by isolation of the cancer cells from the host and by their inactivation, followed by elimination of the tumor (surgery, radiation, chemotherapy) and the reinoculation of the inactivated tumoral cells in the patient, in order to induce an immunological reaction against the surface antigens of the tumor.

Immunotherapy based on such a system of specific recognition is only poorly efficient when applied alone. There may be production of antibodies against the neoplasm but the appearance of a delayed hypersensitivity, believed to be the main immunological method of elimination of residual tumoral cells, is rarely observed (J. Sokal et al.: Nat Cancer Inst, Monograph No. 39, p. 195–198 (1973)).

In addition, this technique is difficult to implement because it entails the collection of cancer cells from the patient (often present under the form of a solid tumor or a suspension) and the re-presentation of these cells, which must be easily inactivated by irradiation and reinoculated into the patient. Moreover, the risk that a patient may be inoculated by incompletely inactivated cancer cells is never totally excluded.

Because of these difficulties, specific immunotherapy is complemented either by an aspecific immunotherapy or else totally abandoned in favour of the latter (G. Mathé et al.: Nat. Cancer Inst. Monograph No. 39, p. 165–175 (1973)).

One form of non-specific immunotherapy has been performed for more than twenty years in the form of the antituberculous vaccine composed of live cells of an attenuated strain of the bovine tubercle bacillus, *Mycobacterium bovis* (strain Calmette-Guerin or BCG ®). The administration of BCG, either systemically or topically, has remarkable effects on the remission of all kinds of human cancers, provided the immune system of the patient be not exhausted and the cancerous mass to be treated be not too substantial. Following a primary treatment of the patient by chemotherapy, irradiation or surgery, maintenance of the patient under remission is favoured by the administration of BCG that stimulates the aspecific immune defenses of the patient and favours the elimination of the residual cancer cells, or else at least controls their multiplication. A similar effect is observed with Corynebacterium and Nocardia, which belong to the same bacterial group (designated MHC group) as mycobacteria. Because of availability, the majority of the applications is made by BCG.

Nevertheless, the secondary (side) effects of the vaccine are not negligible: hyperthermia, chills, nausea, weakness, local infections, articular pain, swelling of wrists and other joints, vomiting and diarrhoea. The secondary effects are counteracted either by administration of salicylate, or, more frequently, by treatment of the patient in discomfort by an antituberculous drug, normally isoniazid.

Another serious objection to the use of live bacilli is the possibility of infecting the patient and to provoke a disseminated bovine tuberculosis, which may sometimes be lethal (M. McKneally et al.: The Lancet, May 7, p. 1003 (1977)) and is also usually treated by an antituberculous drug.

Moreover, great disparities have been observed in the immunotherapeutic effect of BCG, depending on source, storage and processing (J. O Bennett et al.: Cancer Res. 43, p. 4183–4190 (1983)).

The use of tuberculin (PPD, Purified Protein Derivative) for the same immunotherapeutic purpose has been attempted but has not been the object of advanced research endeavours. The motive of this failure of reseachers to explore this possible technique was in part the great variability observed in the effects produced according to the origin of the used PPD, the readily availability of BCG and, above all, the belief that the efficacy of the treatment depended on the viability of the inoculated material (an inert material such as PPD was supposedly less efficacious than live material such as BCG (J. Bennett et al.: Cancer Res., 43, p. 4183–4190 (1983)).

In addition, the hypothesis has recently been formulated that mycobacteria possess the property to induce an immunodepression in the organisms they infect: their use in a living form to potentiate the immune response of cancer patients may, if the immunological defenses of the cancerous recipient are weak, be in vain because the bacilli may in fact increase the immunodepression due to the tumor and may even provoke a generalized infection. Thus, under some conditions, the use of live material may be doubly dangerous.

On the other hand, the capacity that some mycobacterial species possess to reduce the immunity of the host would explain the variations observed in the expected immunopotentiation, when different mycobacterial strains, of variable virulence, are used.

In addition, the occasional necessity to administer antituberculous drugs when BCG is inoculated in cancer patients (McKneally et al.: The Lancet, May 7, p. 1003 (1977)) may lesd to the conclusion that the generally admitted assertion by all clinicians presently implied in this type of treatment, that live bacteria are necessary to obtain the expected immunopotentiating effects, may very well be incorrect.

STATE OF THE ART

Microorganisms of the group MNC (Mycobacteria, Nocardia, Corynebacteria) to which belongs BCG, are complex microorganisms constituted of numerous antigenic structures. For example, *M. tuberculosis*, which was originally believed to be composed of only 11 antigens, is now recognized to be constituted of a much larger number of these antigens. Some of these antigens are common to several genera, i.e. they show a crossed immunological reactivity between organisms belonging to the Corynebacterium, Mycobacterium and Nocardia group (MNC).

Among these antigens, the thermostable macromolecular antigens (TMA) complexes present a distinct interest because they are thermostable, they are potently antigenic and they are common (without being identical) to all the microorganisms belonging to the MNC group.

They have been isolated and characterized by Closs et al. (Scand. J. Immunol. 12, p. 249–263 (1980)); Cochito and Vanlinden (Med. Microb. Immunol. 177, p. 357–367 (1988)); Aboud-Zeid et al. (J. Infect. Dis. 151, p. 170–178 (1985)); Gueur et al. (Scand. J. Immunol. 17, p. 497–506 (1983)). TMA's isolated from different mycobacterial species bear different numbers. For example, the TMA of *M. bovis* is antigen 60 while that of *M. leprae* is antigen 7.

In particular, antigen complex 60 of *M. bovis* and antigen complex 7 of *M. leprae* are very similar (Harboe et al.: Scand. J. Immunol. 8, p. 115–124 (1979)).

The TMA complex is known to be the immunodominant antigen in natural mycobacterial infections. For *M. tuberculosis* and *M. bovis*, most of the antibodies (87.5%) of an infected patient are directed against the TMA complex (Coetsier et al., Clin. Diag. Lab. Immunol. 1(2), p. 139–144 (1994) ). The TMA complex provokes the creation of humoral circulating antibodies and may be used with efficacy as tuberculin and as antituberculous vaccine (U.S. Pat. No. 4,965,192).

The patent applications FR-A-2529462, FR-A-2586280 and GB-A-2,120,548 (RIBI IMMUNOCHEM RESEARCH) dislose the use of pharmaceutical compositions comprising mycobacterial extracts (soluble in pyridine) for the treatment of tumors.

However, these extracts are mostly lipids having a small molecular weight and do not contain the TMA complex which is not soluble in pyridine.

AIMS OF THE INVENTION

The purpose of the present invention is to provide a new immunotherapeutic treatment of cancer, which does not present the drawbacks of the state of the art, which has no or little secondary effects and which is reproducible.

Another purpose of the invention is to obtain a treatment that induces an immune reaction against cancer which is equivalent or superior to that resulting from the vaccinal administration of BCG but is free of the negative secondary effects observed with the latter.

SUMMARY OF THE INVENTION

The present invention concerns a method of treating and/or preventing cancer which comprises administering to a patient an anti-tumor effective amount of a TMA complex and/or a fragment of this TMA complex, each of which is interspecific for the microorganisms belonging to the MNC group and shows after electrophoresis the immunoelectrophoretic precipitation pattern corresponding to that of the antigen complex 60 of *Mycobacterium bovis* Calmette-Guerin bacillus strain (BCG).

Advantageously, said method also comprises administering to the patient a cancer-specific therapeutic agent, preferably non-proliferative tumor cells (made non-proliferative by processes known to the man skilled in the art) and/or tumoral antigens (obtained for example by genetic engineering or by isolation of antigens extracted from tumoral cells).

Advantageously, said method further comprises administering to the patient a separate aspecific therapeutic agent against cancer, chosen among the group consisting of bicatenary nucleic acids, preferably complexed to protamine, vitamin C, a water-in-oil emulsion and/or a mixture thereof.

The phrase "fragment of an TMA complex" means an immunologically active portion of said TMA complex which reacts with an antibody directed against the TMA complex.

The phrase "an anti-tumor effective amount of TMA complex and/or a fragment of this TMA complex" means the BCG amount generally used for the treatment or the prevention of tumors, preferably an amount comprised between $5 \times 10^{-3}$ µg and 5 mg (TMA complex)/ml (saline solution).

DESCRIPTION OF A PREFERRED EMBODIMENT OF THE INVENTION

The present invention relies on the unexpected observation that an effective amount of an antigen (and/or several of its fragments) interspecific for microorganisms belonging to the MNC group (species of the genera Mycobacteria, Nocardia, and Corynebacteria), showing after counterelectrophoresis a pattern of immunoelectrophoretic precipitation corresponding to A60 of *Mycobacterium bovis* strain Bacillus Calmette-Guerin, exhibits a remarkable capacity to control test cancers.

Mycobacterial antigen complex 60, its isolation and the process of obtention of fragments of this complex have been described in EP-0184511.

Antigen complex 60 of *M. bovis* (attenuated strain of Bacillus Calmette-Guerin) is the component of the bacterial cytoplasm, migrating the slowest in an electrophoretic field (1% agarose in Tris-barbital buffer 0.02 M, pH 8.6; 8 volts/cm during one hour at 15° C. in the first dimension and 3 volts/cm during 18 hours at 15° C. in the second dimension; detection of the proteinic components by Coomassie Blue).

This antigen complex 60 may be obtained by the method in which the cellular walls of said organism are destroyed; the cellular debris are discarded, e.g. by centrifugation, and one collects the supernatant containing the cytoplasm; one performs thereafter an exclusion chromatography by passing the supernatant (possibly treated by an RNase or a DNase) containing the cytoplasm on an exclusion gel and one collects the peak of exclusion containing the antigen complex 60 substantially pure form.

The fragments of the antigen complex 60 may be obtained by contacting the antigen complex 60 with a protease or a chemical agent endowed with the function of a protease such as cyanogen bromide; and separating the immunologically active fragments for example from the other fragments, by contact with an adsorbing agent sensitized with an antibody directed against A60 so as to form a "immunologically active fragments-anti-A60 antibodies" complex, which are collected.

An anti-tumor effective amount of antigen complex 60 used for the treatment and/or the prevention of cancer is defined by the effective amount of BCG or purified protein derivative previosly used for the treatment of bladder, skin and lung tumors.

Bladder Tumors.

60 $\mu$g to 120 $\mu$g of antigen complex 60 suspended in 50 ml of a saline solution (0.9% NaCl) may be administered for 2 hours by means of a catheter into the bladder of a patient.

This treatment is done into each week during 6 to 8 weeks.

A systemic treatment (not necessary) may also be used each week by the percutaneous administration of 5 mg BCG or antigen complex 60.

Skin Tumors.

0.5 $\mu$g to 15 $\mu$g in 0.5 ml of saline solution of the antigen complex 60 may be inoculated in skin metastases or used as a general topic application.

Lung Tumors.

2.5 mg to 12 mg in 50 ml of a saline solution may be administrated for the treatment of lung tumors.

A constant in the evaluation of the immunopotentiating power of mycobactarial antigens for the control of cancers in regression is the strong parallelism existing between the effects observed by the same preparations in the treatment of human cancers (G. Mathé et al.: Nat. Cancer Inst. Monograph No. 39, p. 165–175 (1973); J. Sokal et al.: Nat. Cancer Inst. Monograph No. 39, p. 195–199 (1973); J. Bennett et al.: Cancer Res. No. 43, p. 4183–4190 (1983)).

The experimental murine models used in the present invention and representative of human cancers are the following:

- an hepatic carcinoma, the Taper liver tumor (TLT) this murine neoplasmic line is maintained in vitro in a culture medium constituted of RPMI at 37° C. under 5% $CO_2$ and maintained in vivo by successive passages in NMRI mice;
- a mammary carcinoma, strain EMT 6; the cells are maintained in vitro in McCoy medium at 37° C. under 5% $CO_2$ and are propagated in vivo in Balb/c mice;
- a Lewis lung carcinoma (3 Lewis-Lung: 3LL); this neoplasmic strain is propagated in vitro in MEM medium at 37° C. under 5% $CO_2$, and propagated in vivo in C57Bl/6 mice.

The suspensions of tumoral cells are inoculated at different concentrations, by intraperitoneal or intramuscular route. The prophylactic immunotherapeutic treatment consisted in the following applications:

1. Isologous tumoral cells cultured in vitro are inactivated by gamma irradiation in a $^{60}Co$ gamma emettor (Atomic Energy of Canada) with irradiation doses sufficient to induce a drop of viability of $10^7$. The irradiated cells are inoculated by intraperitoneal or intramuscular route at a dose of $10^3$–$10^7$ cells in a phosphate-saline buffer (PBS). The irradiated cells are inoculated in one or several doses, the last dose being normally given 15 days before the inoculation of life isologous neoplasmic cells. One experiment was done where the suspension of irradiated cells was emulsified in oil.

2. Antigen complex 60 or other TMA complexes, obtained from various bacterial species belonging to the MNC group, were inoculated at a dose of 30 $\mu$g/100 $\mu$l/animal in a water-in-oil emulsion. The inoculations took place 30 days and 8 days before the introduction of neoplasmic cells. Sometimes, a third inoculation of TMA complex took place on the day preceding the inoculation of tumoral cells.

3. *M. bovis* strain BCG, was inoculated subcutaneously at a dose of $10^5$ viable cells in suspension in phosphate-saline buffer (PBS), 30 days and 8 days before the inoculation of cancer cells.

4. A solution of bicatenary nucleic acid, sometimes protected by a protamine, was prepared according to known techniques (U.S. Pat. No. 3,679,654) and used at the dose of 40 $\mu$g/animal 30 and 8 days before the tumor challenge. The intraperitoneal inoculation was performed at the same time that the inoculation of isologous irradiated cancer cells, or together with the inoculation of TMA complex.

5. Ascorbic acid (vitamin C) was given in the drinking water of the treated animals during one month before the inoculation of tumoral cells and as long as the tumor-bearing animals were alive.

6. The mean survival time (MST) corresponding to the number of days when the number of dead animals became greater than half of the total number of animals included in the analysed experimental group; the increase in life expectancy, expressed in percentage, compared to controls (ILE); and the incidence of induced experimental cancers, i.e. the long-term cancerous incidence (LTI) are calculated with a mean of 17 animals per analysed experimental group. The various prophylactic agents applied alone at the indicated doses have no incidence on the mortality of the animals, whose life expectancy is identical to the untreated controls.

The invention will be described in a more detailed way in the following examples, which should limit in no way the extent of the invention.

EXAMPLE 1

Table 1 presents the oncologic indexes found for the TLT carcinoma, Taper liver tumor. The tumor challenge was performed by an intraperitoneal or intramuscular inoculation of 1,000 to 100,000 viable cancer cells.

The prophylaxy is realized by irradiated cancerous cells, by antigen complex 60 (A60) extracted from BCG or by the two agents together.

TLT cells are very aggressive: all the inoculated mice die, of which half in a little more than a month, depending on the dose and the route of inoculation. A careful examination of the increase in life expectancy after prophylaxis treatment shows that the prophylaxis is most efficacious when a small dose of cancer cells is inoculated via the intramuscular route (IM). When a large dose of cancer cells is inoculated, the prophylaxy appears more efficacious when the challenge is intraperitoneal because the death of the control animals occurs in less than a month.

TABLE I

| Treatment | Tumoral line | | M.S. Time (days) | INC.L. EXP (%) | LO.T. INC (%) |
|---|---|---|---|---|---|
| 1. TLT Challenge:1,000 viable cells | | | | | |
| none | TLT | IM | 32.5 | 0 | 100 |
| | | IP | 34 | 0 | 100 |
| irradiated cells | TLT | IM | 49 | 50.7 | 100 |
| | | IP | 47 | 38.2 | 100 |
| 2 times A60 (BCG) | TLT | IM | 45 | 38.5 | 100 |
| | | IP | 46.5 | 36.8 | 100 |
| 2 times A60 + cells | TLT | IM | 43.5 | 33.8 | 100 |
| | | IP | 40.5 | 19.1 | 100 |
| 3 times A60 + cells | TLT | IM | 49.5 | 52.3 | 100 |
| | | IP | 47 | 38.2 | 100 |
| 2. TLT Challenge:100,000 viable cells | | | | | |
| none | TLT | IM | 35 | 0 | 100 |
| | | IP | 29 | 0 | 100 |
| irradiated cells | TLT | IM | 45 | 28.5 | 100 |
| | | IP | 44.5 | 53.4 | 100 |
| 2 times A60 (BCG) | TLT | IM | 39.5 | 12.8 | 100 |
| | | IP | 43.5 | 50 | 100 |
| 2 times A60 + cells | TLT | IM | 40 | 14 | 100 |
| | | IP | 42 | 45 | 100 |
| 3 times A60 + cells | TLT | IM | 50 | 43 | 100 |
| | | IP | 52 | 79 | 100 |

The prophylactic treatments prolong the mean survival time of the animals and their life expectancy is increased but they eventually all die. The irradiated cells (specific immunotherapy) have a protecting effect slightly superior to antigen complex 60 (aspecific immunotherapy). The best protective effect seems to occur when the two treatments are given jointly.

EXAMPLE 2

Table II gives the oncologic indexes observed with the EMT 6 mammary carcinoma. A dose of 100,000 viable cells was inoculated intramuscularly. The prophylactic treatment consists in a specific treatment with irradiated cells and an aspecific treatment induced either by antigen complex 60 of BCG inoculated twice or thrice, following the protocol outlined in example 1, or else by viable BCG cells (100,000 live cells in 100 µl, inoculated twice subcutaneously before the tumoral challenge). A prophylaxy applying the two approaches at the same time was also tested.

TABLE II

| Treatment | Tumoral line | M.S. TIME (days) | INC.L.EXP (%) | LO.T.INC (%) |
|---|---|---|---|---|
| none | EMT 6 | 73 | 0 | 100 |
| irradiated cells | EMT 6 | 78 | 6.8 | 100 |
| 2 times A60 (BCG) | EMT 6 | 86.5 | 18.5 | 40 |
| 2 times A60 + cells | EMT 6 | 84.5 | 15.7 | 20 |
| 3 times A60 + cells | EMT 6 | — | 100 | 0 |
| 2 times BCG | EMT 6 | 57.5 | −21.2 | 60 |
| 2 times BCG + cells | EMT 6 | 71.5 | −2 | 40 |

The values reported in the oncological indexes are of course calculated only on mice which have developed a tumor.

The tumor is very potent and all the control mice inoculated and not prophylactically treated, die. The mean survival time of control animals is 73 days, which is clearly longer than the one observed with the liver tumor used in the first example.

The aspecific treatment by A60 is far superior to the specific treatment by irradiated cells: all the mice treated with the irradiated cells die whereas two inoculations of A60 allowed for the survival of 60% of the mice inoculated with tumoral cells. A prophylactic treatment based on the two methods applied at the same time is 100% efficacious at when three antigen complex 60 inoculations are applied: no mouse dies from cancer.

BCG is clearly inferior to antigen complex 60 for the prophylaxis, with or without addition of irradiated cells. One must note the following phenomenon: the BCG treatment is efficacious in some cases and a certain proportion of mice (40% in this experiment) survive; however, when the treatment is not efficacious and does not stop the progress of the cancer, the increase in life expectancy is reduced and the tumor-bearing mice treated with BCG die faster than the controls (diminution of 21.2 days of the life expectancy).

It seems that BCG possesses an immunological effect inverse of that expected: in some ceses it seems to favour the progression of the tumor instead of retarding it.

EXAMPLE 3

In this example on the prophylactic effect of A60 extracted from BCG on the Lewis lung carcinoma (3LL), the experimental protocols applied in the former examples were repeated.

TABLE III

| Treatment | Tumoral line | M.S.TIME (days) | L.EXP.LO (%) | LO.T.INC (%) |
|---|---|---|---|---|
| none | 3LL | 37.5 | 0 | 80 |
| irradiated cells | 3LL | 39 | 4 | 90 |
| 2 times A60 (BCG) | 3LL | 42 | 11 | 30 |
| 2 times A60 + cells | 3LL | 62.5 | 60 | 20 |

The oncological indexes are of course calculated only on the mice which developed a tumor.

The tumor is not very efficient and 20% of the control animals inoculated with 100,000 viable cells survive. on the other hand, the mean survival time of the cancerous animals is little more than a month. Antigen complex 60 used prophylactically is much superior to the specific treatment using isologous irradiated cells (70% survival versus 10%) and a combined treatment still further increases life expectancy (67 days instead of 12) as well as the mean survival time.

These various examples show that A60 presents an effect superior to that of BCG in the aspecific immunoprophylactic treatment of cancers, that the number of antigen complex 60 doses administered is important, that the effect is observed with various tumors (liver, mammary gland and lung) and that the adjunction of a specific prophylaxy further increases the performance of the treatment.

EXAMPLE 4

Tumor EMT 6 is a choice material for the study of the effect of prophylactic agents because the incidence is 100% whereas the growth of the tumor is sufficiently low (mean survival time of the cancerous animals of about 75 days) to observe liminary activities.

One extracts the TMA complex of various mycobacterial species, of Nocardia and of *Corynebacterium parvum* and injects the extracts prophylactically in two doses of 30 µg/100 µl/animal, administered subcutaneously in a water-in-oil emulsion 30, 8 and 1 days before the tumor challenge (EMT 6, 100,000 viable cells/100 µl/animal; IM). Each experimental group is composed of 20 animals. The oncological indexes are listed in table IV.

TABLE IV

| | Oncological indexes | | |
|---|---|---|---|
| Treatment | M.S.TIME (days) | INC.L.EXP (%) | LO.T.INC (%) |
| none | 77 | 0 | 100 |
| 2 times TMA complex of BCG | 83 | 7.8 | 40 |
| M. vaccae | 91 | 18.2 | 35 |
| M. smegmatis | 86 | 11.7 | 38 |
| M. paratuberculosis | 81 | 5.2 | 40 |
| M. tuberculosis | 84 | 9.1 | 45 |
| M. xenopi | 83 | 7.8 | 40 |
| Nocardia | 81 | 5.2 | 45 |
| C. parvum | 83 | 7.8 | 40 |

The TMA complex extracted from the different species belonging to the MNC group have about the same prophylactic effects. This analysis confirms the previous observations showing that it is the TMA family of antigens at a whole that possesses immunomodulating properties useful for the immunoprophylaxis of cancer.

One observes an accentuated prophylactic effect with TMA complex extracted from M. vaccae than with other antigens: the incidence of cancer is slightly inferior and the life expectancy is slightly longer. These observed effects are statistically insignificant but it is possible that extracts obtained from particular mycobacterial species maybe more or less efficient according to the treated tumor.

EXAMPLE 5

Other immunopotentiators than isologous irradiated cells may be used jointly with TMA complex to obtain a still better prophylactic effect.

1. Poly (I:C) complexed with a protamine according to known techniques (U.S. Pat. No. 3,679,654) is a potent immunopotentiator as well as an excellent promoter of interferon gamma.

2. TMA complexes have been, in the former examples, systematically solubilized in an aqueous phase emulsified in an equal volume of mineral oils. This water-in-oil emulsion represents a whole class of immobilizing agents of the antigen (water-in-oil emulsion, calcium carbonate, aluminium phosphate, latex, liposomes, all well known to the man skilled in the art), that potentiate the immune response against the antigen contained or included or fixed on these agents. A combination of these two additional aspecific immunopotentiators has been tested with irradiated cells and with antigen complex 60 in the following manner.

Antigen complex 60 is inoculated 30, 8 and 1 days before the injection of tumoral cells, according to the protocols previously applied. The antigen complex is solubilized at 30 µg/50 µl of an isotonic aqueous buffer or at 30 µg/100 µl of a water-in-oil emulsion. The poly (I:C) is solubilized at 40 µg/100 µl of an isotonic aqueous solution or in 200 µl of an emulsion, inoculated 30 and 8 days before the injection of tumoral cells. The isologous irradiated cells are suspended in a buffer aqueous isotonic solution or in twice the volume of an emulsion and inoculated 15 days before the challenge.

Table V gives the oncological indexes found for EMT 6 carcinoma (IM challenge of 100,000 cells) in animals prophylactically treated by these various immunopotentiators.

TABLE V

| | Oncological indexes | | |
|---|---|---|---|
| Treatment | M.S.TIME (days) | INC.L.EXP (%) | LO.T.INC (%) |
| none | 74 | — | 100 |
| irradiated cells in aqueous phase | 79 | 6.7 | 100 |
| in emulsion | 87 | 17.5 | 70 |
| A60 | 78 | 5.4 | 80 |
| in aqueous phase | | | |
| in emulsion | 89 | 20 | 40 |
| 40 µg poly (I:C) | 78 | 5.4 | 80 |
| in aqueous phase | | | |
| in emulsion | 91 | 23 | 35 |
| A60 + poly (I:C) | 90 | 21.6 | 50 |
| in aqueous phase | | | |
| in emulsion | 94 | 27 | 20 |
| A60 + poly (I:C) + cells | 110 | 48.6 | 40 |
| in aqueous phase | | | |
| in emulsion | — | 100 | 0 |

Compared to water-in-oil emulsions, the absence of an emulsion diminishes very significantly the effect of the different anti-cancer agents applied. One observes however, even in an aqueous solution, a synergy between antigen complex 60 and poly (I:C): the increase in life expectancy is doubled. This synergy is considerably amplified by the emulsification of the agents, with an increased number of animals which do not develop tumors. Moreover, the immunopotentiating system composed of irradiated cells suspended in an emulsion, plus antigen complex 60 and poly (I:C) in emulsion, is the most effictive, with a protection against tumor growth extended to all the treated mice.

EXAMPLE 6

Vitamin C (ascorbic acid) is an agent known to influence and increase the resistance to infectious agents. Introduced in the diet of cancerous animals, it is known that vitamin C significantly contributes to the regression of tumors. Vitamin C was distributed in the drinking water of the animals, at the dose of 1.23 g/l, changed every two or three days, to determine its effect on the development of a tumoral challenge EMT 6 cells (100,000 cells, IM) in mice preventively treated with different anti-tumoral agents.

Poly (A:U) solubilized in an aqueous phase thereafter emulsified in oil is used instead of poly (I:C), following the protocol identical to the one already described. The other agents are also used following the previously described protocols, i.e. in a water-in-oil emulsion. Results are given in table VI.

TABLE VI

| Challenge EMT 6 (100,000 cells, IM) | | | |
|---|---|---|---|
| | Oncological indexes | | |
| Treatment | M.S.TIME (days) | INC.L.EXP (%) | LO.T.INC (%) |
| none | 65 | — | 100 |
| 2 times A60 (BCG) | 69 | 6 | 30 |
| 2 times A60 with vitamin C | 83 | 28 | 20 |
| 2 times A60 + poly (A:U) | 98 | 51 | 20 |

TABLE VI-continued

Challenge EMT 6 (100,000 cells, IM)

| | Oncological indexes | | |
|---|---|---|---|
| Treatment | M.S.TIME (days) | INC.L.EXP (%) | LO.T.INC (%) |
| 2 times A60 + poly (A:U) with vitamin C | 107 | 65 | 10 |
| 2 times A60 + poly (A:U) + irradiated cells with vitamin C | — | 100 | 0 |

The incidence of cancer is reduced, for each treatment, each time that vitamin C s added to this treatment. One also observes a substantial increase in life expectancy in presence of vitamin C. With A60 alone, the incidence is reduced from 30% to 20% and the increase in life expectancy of cancerous animals is prolonged from 6 to 26 days when they receive vitamin C. When the treatment consists of A60 and bicatenary nucleic acid emulsified in oil, the incidence is much reduced (only 10% of the animals develop a tumor). The effect obtained with this treatment, completed with isologous irradiated cancer cells in the presence of vitamin C, is still more favourable and is comparable to the results observed in examples 2 and 5, where the totality of the animals treated were rendered immune to the tumor challenge. This observation is of course valid only for this precise experimental murine models but the correlation systematically observed between experiment models and the prophylactic effects observed in the clinic make the observation very interesting.

EXAMPLE 7

A similar analysis of the effect of antigen complex 60 (BCG), either alone or in the presence of poly (I:C), with or without the inclusion of vitamin C in the drinking water, has been carried out, using a tumor challenge with the tumor line TLT, which is more virulent than the tumor line EMT 6 used in example 6, in that the animals inoculated with tumoral cells die within a little more than 45 days (mean survival time: 46.5 days).

The applied experimental conditions are those of example 6 with the nucleic acid bicatenary chain poly (I:C) and A60 *M. bovis* inoculated three times, at 30, 7 and 1 days before the tumoral challenge ($5 \times 10^5$ viable TLT cells, inoculated via the intramuscular route). Results are given in table VII.

TABLE VII

Challenge TLT (500,000 cells, IM)

| | Oncological indexes | | |
|---|---|---|---|
| Treatment | M.S.TIME (days) | INC.L.EXP (%) | LO.T.INC (%) |
| none | 46.5 | 0 | 100 |
| 3 times A60 (BCG) | 54.5 | 17 | 100 |
| 3 times A60 with vitamin C | 68.5 | 47.3 | 100 |
| 3 times A60 + poly (I:C) | 61.5 | 32.2 | 100 |
| 3 times A60 + poly (I:C) with vitamin C | 70.5 | 51.6 | 100 |

The animals inoculated with tumor cells all die, with a mean survival time of 46.5 days, The anti-tumoral treatments applied do not affect the survival of the tumor-bearing animals, as all die, but the effect of the treatments is reflected in the increased survival time of the test animals.

While antigen complex 60 administered 3 times alone shows little effect, with a prolongation of the time of survival of 17%, the addition of poly (I:C) and/or vitamin C increases the survival time significantly, the maximum prolongation observed being 51.6% when the three treatments are given together.

What is claimed is:

1. Method of treating a cancer patient which comprises administering to said patient an anti-tumor effective amount of at least one of a water-soluble thermostable macromolecular antigen complex which is interspecific for microorganisms of the Mycobacteria, Nocardia, and Corynebacteria group and which exhibits after electrophoresis an immunoelectrophoretic precipitation pattern corresponding to that of the antigen complex 60 of the *Mycobacterium bovis* Calmette Guerin Bacillus strain, or an immunogenic fragment of such a complex.

2. Method according to claim 1, which comprises the additional step of administering to said patient a therapeutic agent specific against the patient's cancer.

3. Method according to claim 2, wherein said therapeutic agent specific against cancer is selected from the group consisting of a tumoral antigen and a non-proliferative tumor cell.

4. Method according to claim 1, which comprises the additional step of administering to said patient a separate therapeutic agent which is non-specific against the patient's cancer.

5. Method according to claim 4, wherein said non-specific therapeutic agent is at least one member of the group consisting of bicatenary nucleic acids, bicatenary nucleic acids complexed to protamine, vitamin C, and a water-in-oil emulsion as a carrier for said complex or fragment thereof.

6. Method according to claim 2, which comprises the additional step of administering to said patient a separate therapeutic agent which is non-specific against the patient's cancer.

7. Method according to claim 6, wherein said non-specific therapeutic agent is at least one member of the group consisting of bicatenary nucleic acids, bicatenary nucleic acids complexed to protamine, vitamin C, and a water-in-oil emulsion as a carrier for said complev or fragment thereof.

8. The method of claim 1 wherein said treatment is administered to said cancer patient after treatment of said patient selected from the group consisting of surgical excision, chemotherapy, and radiation.

9. The method of claim 1 wherein said water-soluble thermostable macromolecular antigen complex administered to said patient is antigen complex 60 of the *Mycobacterium bovis* Calmette Guerin Bacillus strain.

* * * * *